(12) United States Patent
Milijasevic et al.

(10) Patent No.: US 8,777,951 B2
(45) Date of Patent: Jul. 15, 2014

(54) MINIMALLY INVASIVE TISSUE PROSTHESIS IMPLANTING DEVICE AND METHOD

(75) Inventors: Zoran Milijasevic, Bayview (AU); Ashish Diwan, Sydney (AU)

(73) Assignee: SpineCell Private Ltd

( * ) Notice: Subject to any disclaimer, the term of this patent is extended or adjusted under 35 U.S.C. 154(b) by 1102 days.

(21) Appl. No.: 12/739,375

(22) PCT Filed: Oct. 23, 2007

(86) PCT No.: PCT/AU2007/001608
§ 371 (c)(1),
(2), (4) Date: Sep. 23, 2010

(87) PCT Pub. No.: WO2008/061288
PCT Pub. Date: May 29, 2008

(65) Prior Publication Data
US 2011/0208253 A1  Aug. 25, 2011

(51) Int. Cl.
*A61B 17/70* (2006.01)
*A61F 2/44* (2006.01)
*A61F 2/30* (2006.01)
*A61F 2/46* (2006.01)
*A61B 5/04* (2006.01)

(52) U.S. Cl.
CPC ............ *A61F 2/441* (2013.01); *A61F 2250/008* (2013.01); *A61F 2230/0069* (2013.01); *A61F 2002/444* (2013.01); *A61F 2002/30698* (2013.01); *A61F 2002/30235* (2013.01); *A61F 2002/30069* (2013.01); *A61F 2002/4685* (2013.01); *A61F 2002/4627* (2013.01); *A61B 5/04* (2013.01); *A61F 2002/30777* (2013.01); *A61F 2/4611* (2013.01)
USPC ....................................................... 606/86 A

(58) Field of Classification Search
CPC .. A61F 2/4611; A61F 2/441; A61F 2002/444
USPC .................. 606/17.11–17.16, 86 A, 914; 623/17.11–17.16
See application file for complete search history.

(56) References Cited

U.S. PATENT DOCUMENTS

| 7,156,877 | B2 | 1/2007 | Lotz et al. | |
|---|---|---|---|---|
| 7,879,097 | B2 * | 2/2011 | Lambrecht et al. | ........ 623/17.11 |
| 2005/0033441 | A1 | 2/2005 | Lambrecht et al. | |

FOREIGN PATENT DOCUMENTS

| WO | WO 02/17825 | A2 | 3/2002 |
|---|---|---|---|
| WO | WO 2006/118930 | A2 | 11/2006 |

* cited by examiner

*Primary Examiner* — Sameh Boles
(74) *Attorney, Agent, or Firm* — Jerry R Potts

(57) ABSTRACT

A tissue prosthesis delivery device (10) includes an elongate, tubular introducer element (12), the element having a tissue piercing distal end (14) with an opening (16) arranged proximally of the distal end (14). A closure member (18) is associated with the introducer element (12) for opening and closing the opening (16) of the introducer element (12). An expansible prosthesis envelope (20) is received in a collapsed configuration within the tubular introducer element (12) to be deployed laterally of the introducer element (12) through the opening (16).

14 Claims, 6 Drawing Sheets

MINIMALLY INVASIVE TISSUE PROSTHESIS IMPLANTING DEVICE AND METHOD

CROSS-REFERENCE TO RELATED APPLICATIONS

The present application is a national phase application under 35 U.S.C. §371 of International Patent Application No. PCT/AU2007/001608 filed on Oct. 23, 2007, the contents of which are incorporated herein by reference in their entirety.

FIELD

This invention relates, generally, to implanting a tissue prosthesis, such as an intervertebral disc nucleus prosthesis, and, more particularly, to a tissue prosthesis delivery device and to a system for, and a method of, implanting a tissue prosthesis.

BACKGROUND

Various techniques have been proposed for dealing with age or injury related intervertebral disc degeneration. Two techniques in use are disc removal and fusion. Both of these techniques involve major invasive surgery with the related risks. More recently, another technique employed has involved the replacing of a degenerative disc with an artificial disc. This, once again, is carried out using major invasive techniques.

An intervertebral disc comprises two parts, an annulus fibrosis surrounding a nucleus pulposus. The intervertebral disc cooperates with end plates of the vertebrae between which it is sandwiched. Still more recently, techniques have been proposed to replace only the nucleus pulposus of the disc in circumstances where the degeneration is detected at a sufficiently early stage. Such techniques may be able to be performed in a minimally invasive manner.

A need exists generally when implanting a tissue prosthesis to cause as little trauma to the surrounding tissue as possible. For example, in the case of an intervertebral disc, one would aim, when doing minimally invasive replacement of a degenerative nucleus pulposus, to minimise trauma to the surrounding annulus fibrosis of the disc.

SUMMARY

According to a first aspect of the invention, there is provided a tissue prosthesis delivery device which includes
an elongate, tubular introducer element, the element having a tissue piercing distal end with an opening arranged proximally of the distal end;
a closure member associated with the introducer element for opening and closing the opening of the introducer element; and
an expansible prosthesis envelope received in a collapsed configuration within the tubular introducer element to be deployed laterally of the introducer element through the opening.

The device may include a tissue removal mechanism carried in the introducer element to be extended through the opening to aid in tissue removal at a site in the patient's body where the prosthesis is to be implanted.

The tissue removal mechanism may include a filamentary element which is extended from the opening to effect tissue removal. The filamentary element may be extended in a bowed configuration from the opening. Tissue removal may then be effected by rotating the introducer element while the filamentary element is in its bowed configuration.

Further, the tissue removal mechanism may be conductive to be energised to effect tissue removal. More particularly, the tissue removal mechanism may be energised with RF energy to effect tissue removal.

The device may include a control member for controlling operation of the tissue removal mechanism. The control member may be removably mounted to a proximal end of the introducer element, the tissue removal mechanism being removable for allowing deployment of the prosthesis envelope.

The envelope may be an elastically deformable envelope. The envelope may be of an elastomeric material, more particularly, a silicone material.

The introducer element may be conductive to stimulate surrounding nerves in the patient's body electrically to evoke a response to reduce the likelihood of causing nerve damage as the introducer element is manoeuvred through the patient's body.

The closure member may be a sleeve displaceably arranged relative to the introducer element. The sleeve may be axially or rotatably displaceable relative to the sleeve. In the latter case, the sleeve may define a distal slot which is brought into register with the opening when the sleeve is rotated relative to the introducer element.

The device may include a filler tube in the introducer element with the envelope being mounted on a distal end of the filler tube and a proximal end of the filler tube being connectable to a supply of filler material.

Further, the device may include a connection to a withdrawal device for withdrawing fluid from the envelope.

According to a second aspect of the invention, there is provided a tissue prosthesis delivery device which includes
an elongate, tubular introducer element, the element having a tissue piercing distal end with an opening arranged proximally of the distal end;
a closure member associated with the introducer element for opening and closing the opening of the introducer element; and
a tissue removal mechanism carried in the introducer element to be extended through the opening to aid in tissue removal at a site in the patient's body where the prosthesis is to be implanted.

According to a third aspect of the invention, there is provided a tissue prosthesis delivery device which includes
an elongate, tubular introducer element, the element having a tissue piercing distal end with an opening arranged proximally of the distal end;
a closure member associated with the introducer element for opening and closing the opening of the introducer element; and
at least the distal end of the introducer element being conductive to stimulate surrounding nerves in the patient's body electrically to evoke a response to reduce the likelihood of causing nerve damage as the introducer element is manoeuvred through the patient's body.

The invention extends also to a system for implanting a tissue prosthesis, the system including
a tissue prosthesis delivery device as described above;
a sensor pack attachable to the patient's body for sensing a response from any stimulated nerves; and
an enunciator for alerting a clinician to a stimulated nerve.

The sensor pack may include a plurality of sensors, each of which is attachable at a predetermined location on the patient's body.

The enunciator may include an electromyograph (EMG).

According to a fourth aspect of the invention, there is provided a method of implanting a tissue prosthesis, the method comprising minimally invasively introducing an introducer element into a patient's body using a tissue piercing distal end of the introducer element and the introducer element being tubular and carrying an expansible prosthesis envelope in a collapsed state within the introducer element proximally of the distal end;

at a site in the patient's body at which the prosthesis is to be formed, deploying the envelope through an opening defined, proximally of the distal end, in a side wall of the introducer element by charging a filler material into an interior of the envelope to cause the envelope to expand and conform to a cavity at the site in the patient's body; and detaching the expanded envelope from the introducer element and withdrawing the introducer element.

The method may include energising at least the distal end of the introducer element to evoke a response from surrounding nerves of the patient as the introducer is manoeuvred to the site to inhibit damage to the nerves.

The method may include, initially, removing tissue from the site using the introducer element. The introducer element may include a tissue removal mechanism and the method may include extending the tissue removal mechanism through the opening of the introducer element and manipulating the introducer element to facilitate removal of tissue from the site by the tissue removal mechanism. Further, the method may include energising the tissue removal mechanism with RF energy to aid in tissue removal.

The method may include, after tissue removal has been completed, removing the tissue removal mechanism from the introducer element to allow the prosthesis envelope to be expanded through the opening of the introducer element.

The opening may be closed by a closure member and the method may include displacing the closure element relative to the introducer element when the introducer element is in the desired position relative to the site to place the interior of the introducer element in communication with the site.

The method may include expanding the envelope to a size greater than a cavity which the envelope is to fill so that, upon removal of the introducer element after filling of the envelope, the envelope conforms to the size of the cavity.

DETAILED DESCRIPTION OF EXEMPLARY EMBODIMENT

Figure 1:
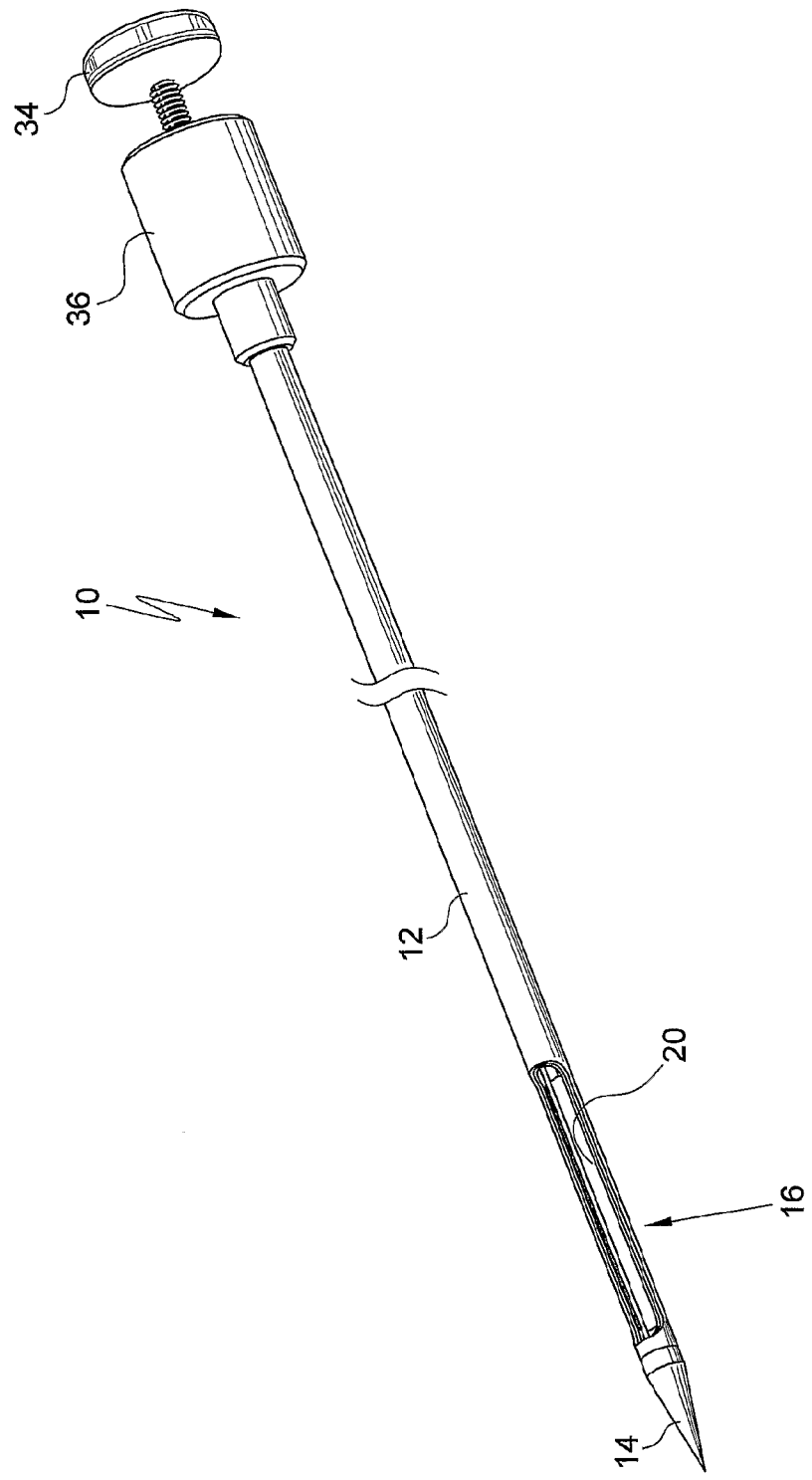
FIG. 1 shows a three dimensional view of an embodiment of a tissue prosthesis delivery device.

In the drawings, reference numeral 10 generally designates an embodiment of a tissue prosthesis delivery device. The device 10 includes an elongate tubular introducer element 12. The element 12 has a tissue piercing distal end in the form of a pointed tip 14 with an opening 16 (shown more clearly in FIGS. 3, 4 and 7 of the drawings), arranged proximally of the tip 14.

A closure member 18 is associated with the introducer element 12 for openably closing the opening 16 of the introducer element 12.

An expansible prosthesis envelope 20 is received in a collapsed configuration in the introducer element 12 to be deployed laterally of the introducer element 12 through the opening 16, as will be described in greater detail below.

The delivery device 10 is intended particularly for use in intervertebral disc nucleus replacement. It will, however, be appreciated that the delivery device 10 could be used in other applications. However, for ease of explanation, the delivery device 10 will be described with reference to its application to intervertebral disc nucleus replacement.

Figure 2:
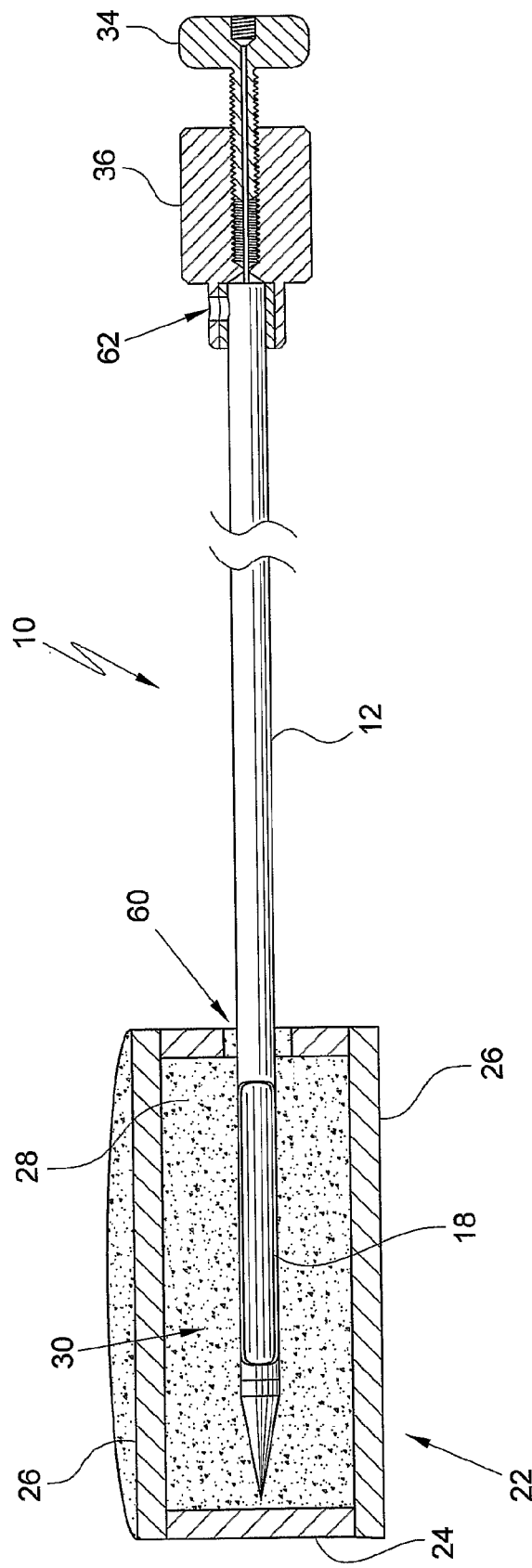
FIG. 2 shows a schematic sectional side view of the delivery device, in use.
Figure 8:
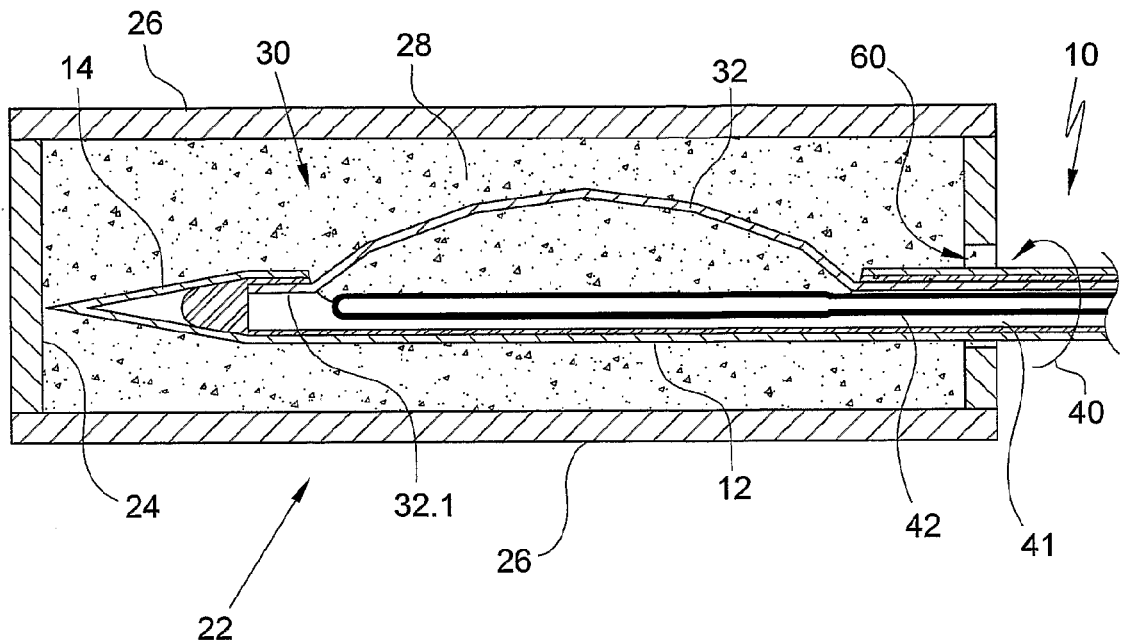
FIG. 8 shows a schematic sectional side view of the distal portion of the delivery device in situ with the tissue removal mechanism in its extended, operative position.

The intervertebral disc is shown schematically at 22 in FIGS. 2 and 8 of the drawings. The disc 22 includes an annulus fibrosis, or annulus 24. The annulus 24 is sandwiched between end plates 26 of adjacent vertebrae. The annulus 24 and the end plates 26 define a cavity 28 in which a nucleus 30 is contained. Generally, with a diseased intervertebral disc 22, the nucleus 30 degenerates and leaks through the annulus 24. Thus, for replacement of the nucleus 30, it may, in certain circumstances, not be necessary to remove nuclear tissue from within the disc 22.

The delivery device 10 includes a tissue removal mechanism in the form of a nucleotomy wire 32. The nucleotomy wire 32 is mounted longitudinally in the tubular element 12 and can be extended out of the opening 16. The nucleotomy wire 32 overlies the tissue prosthesis envelope 20 when the tissue prosthesis envelope 20 is in its collapsed configuration. The nucleotomy wire 32 is controlled by a control member 34 (FIG. 1). The control member 34 cooperates with a boss 36 arranged at a proximal end of the introducer element 12.

Figure 3:
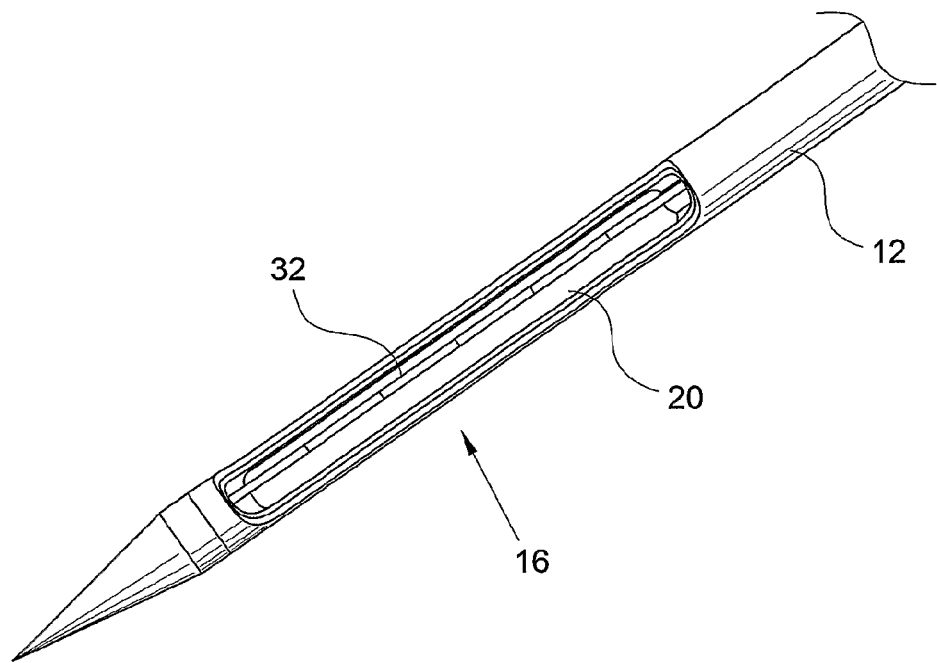
FIG. 3 shows a three dimensional view of a distal portion of the delivery device with its opening open.
Figure 4:
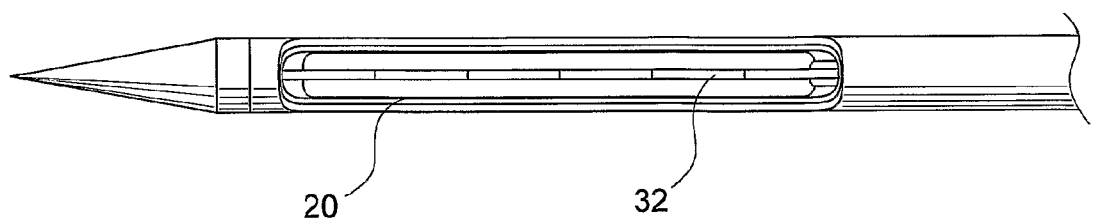
FIG. 4 shows a plan view of a distal portion of the delivery device with its opening open.
Figure 5:
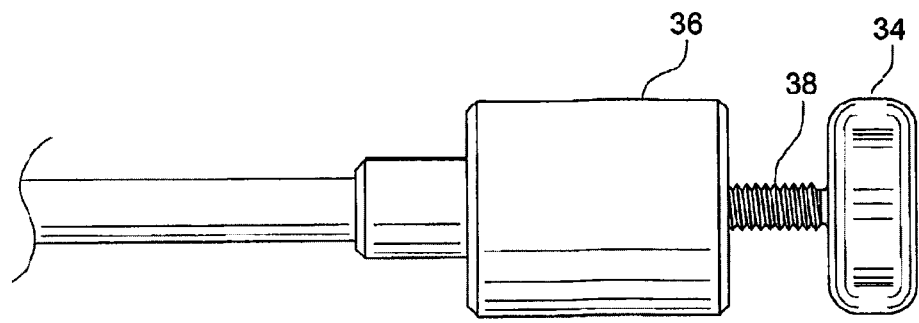
FIG. 5 shows a control member of the delivery device in a first position.
Figure 6:
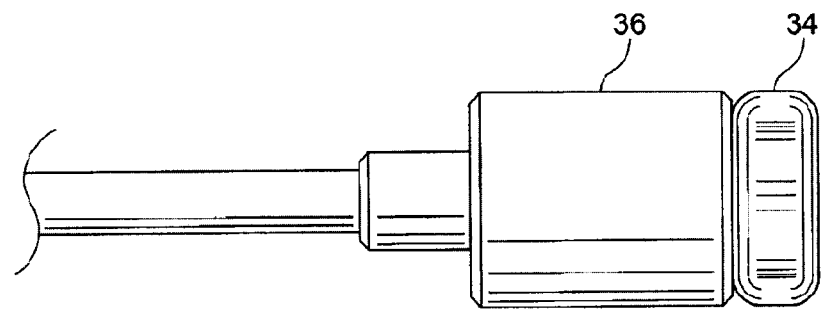
FIG. 6 shows the control member in a second position.
Figure 7:
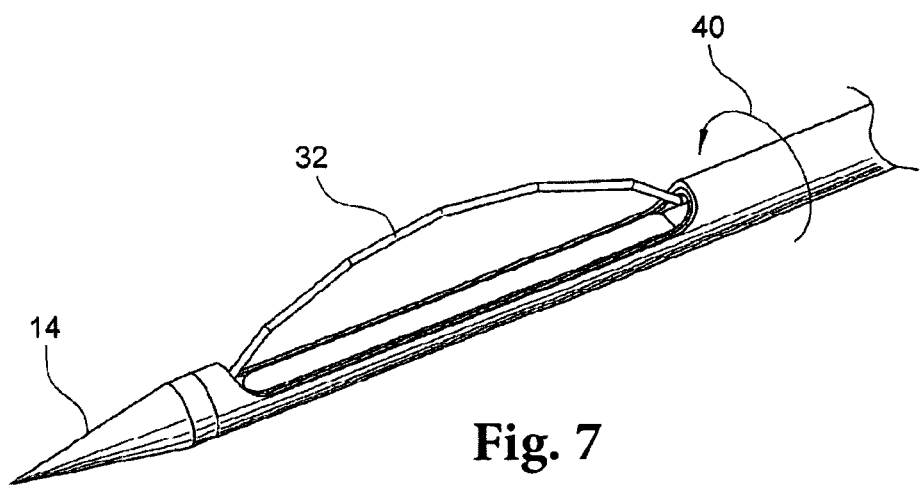
FIG. 7 shows a three dimensional view of the distal portion of the delivery device with a tissue removal mechanism in an extended, operative position.

As shown more clearly in FIGS. 5 and 6 of the drawings, when the nucleotomy wire 32 is in a retracted configuration, as shown in FIGS. 2 to 4 of the drawings, the control member 34 is in an extended position relative to the boss 36. The control member 34 has a threaded shank (FIG. 5). By screwing the control member 34 into the boss 36, the nucleotomy wire 32 is urged out of the opening 16 into a bowed configuration as shown in FIG. 7 of the drawings. In this configuration, when the distal part of the delivery device 10 is within the cavity 28 of the disc 22, by rotating the introducer element 12 about its longitudinal axis, as shown by arrow 40 (FIG. 7), as well as by moving it longitudinally to and fro nuclear material can be removed. In this regard, it is to be noted that, if desired, the nucleotomy wire 32 can be fabricated to be conductive. Thus, the nucleotomy wire 32 can, additionally, be energised with RF energy to aid in removal of nuclear material from within the cavity 28 of the disc 22.

As shown in FIG. 8 of the drawings, a distal end 32.1 of the nucleotomy wire 32 is fixed in position within the tip 14 of the introducer element 12. Further, the tip 32.1 of the nucleotomy wire 32 is shaped to encourage bowing of the nucleotomy wire 32 when the control member 34 is screwed into the boss 36.

The nucleotomy wire 32 is able to be removed from the introducer element 12 by unscrewing the control member 34 from the boss 36 completely and withdrawing it.

A lumen 41 (FIG. 8) of the introducer element 12 functions as an evacuation tube so that, when nuclear material is dislodged by the nucleotomy wire 32, it can be withdrawn from the cavity 28 of the disc 22 through the opening of the 16 of the introducer element 12 by suction.

As shown more clearly in FIG. 8 of the drawings, the nucleotomy wire 32 is mounted distally of a filler tube 42 which extends through the introducer element 12. A proximal end of the filler tube 42 is connected, in use, to a source of filler material (not shown). The filler tube 42 is, optionally, of a flexible material to render it collapsible.

Figure 9:
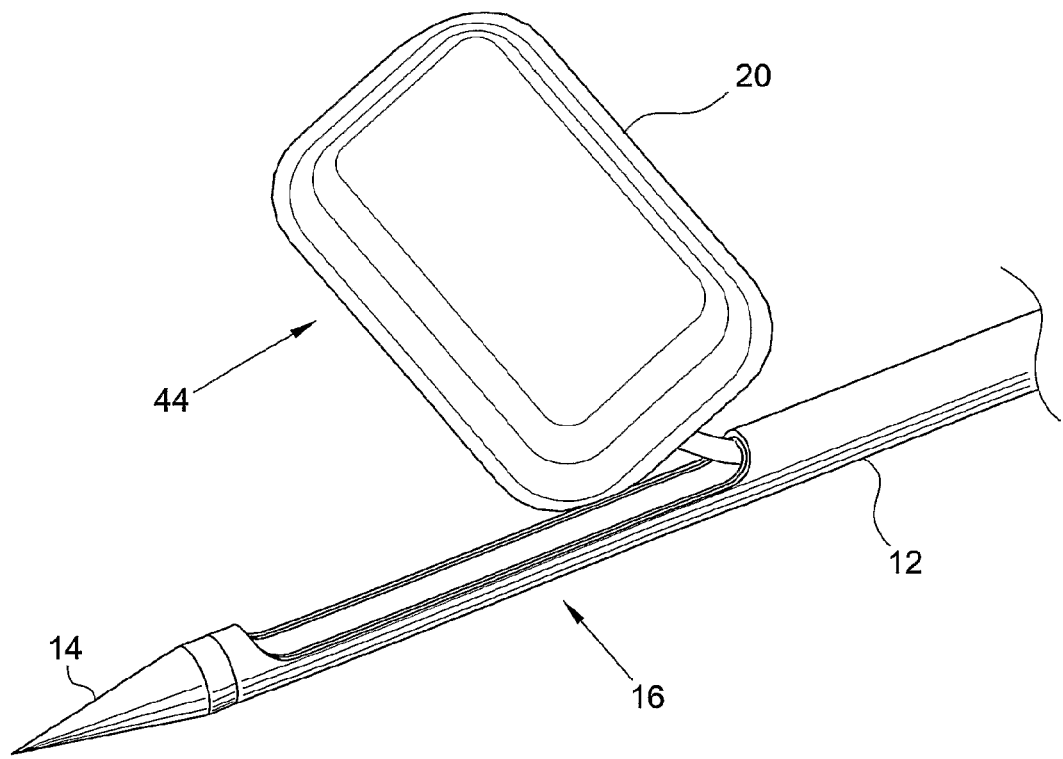
FIG. 9 shows a three dimensional view of the delivery device with a tissue prosthesis envelope expanded and ready to be released from the delivery device.

Once the nucleotomy wire 32 has been removed from the introducer element 12, the envelope 20 can be expanded by charging filler material into the envelope 20 to form a nuclear prosthesis 44 (FIG. 9).

The tip 14 of the introducer element 12 of the device 10 is a conductive tip 14. The tip 14 is, in use, energised when the introducer element 12 is inserted into the patient's body so that the tip 14 stimulates surrounding nerves and evokes a response from the nerves.

Figure 10:
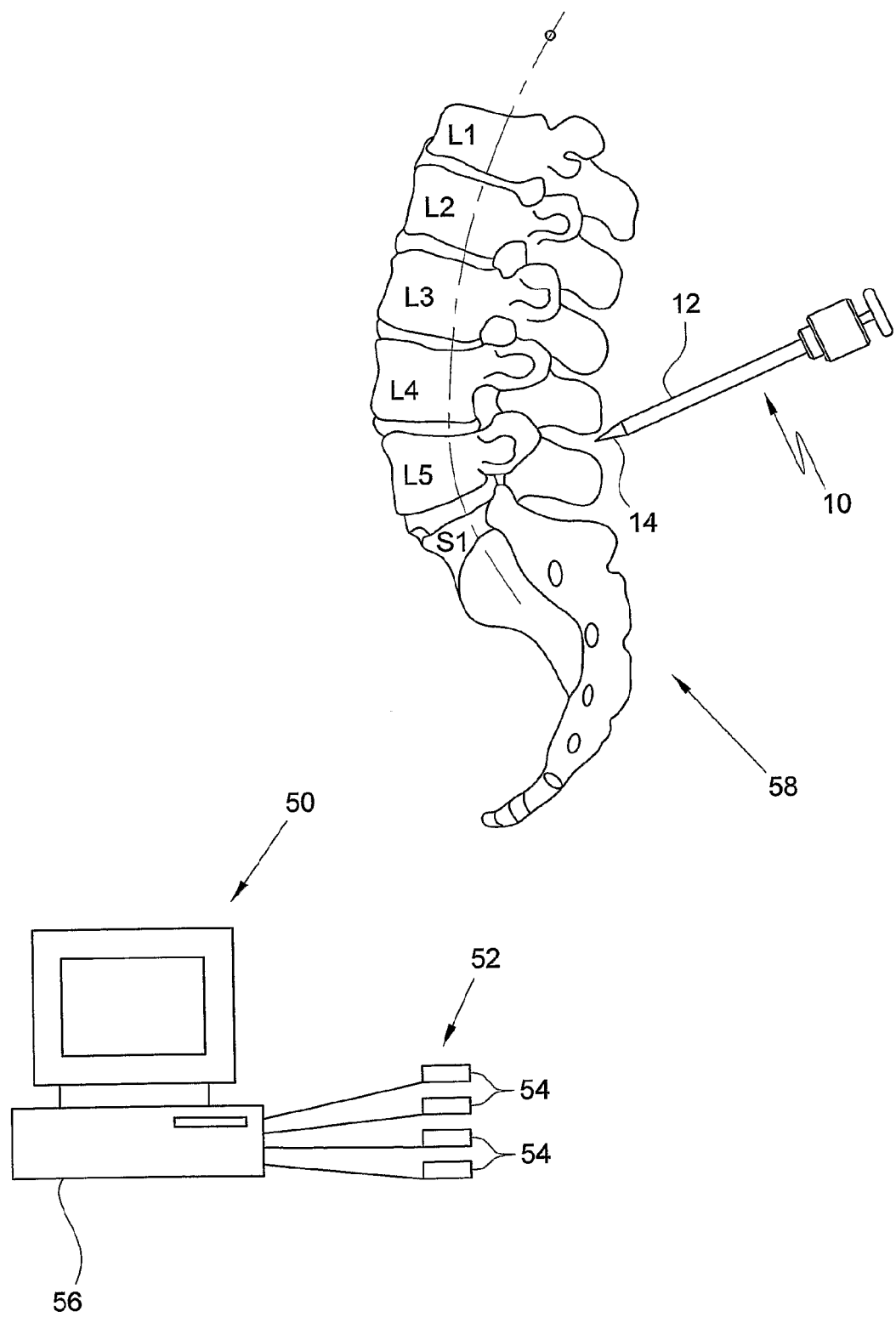
FIG. 10 shows a schematic representation of an embodiment of a system for implanting a tissue prosthesis.

In FIG. 10 of the drawings, reference numeral 50 generally designates an embodiment of a system for inserting a tissue prosthesis. The system 50 includes the delivery device 10. The system 50 further includes a sensor pack 52 comprising a plurality of sensors 54. Typically, four such sensors 54 are provided which are attached at various locations on a patient's body and which pick up muscle contractions arising from stimulation of nerves. These sensors 54 are associated with the muscles stimulated by nerves radiating from the spinal cord in the lumbar region of the spine and are typically in the legs of the patient. Thus, the sensors 54 are attached to the patient's legs prior to insertion of the delivery device 10 into the patient's body.

The sensor pack 52 is connected to an enunciator 56 shown, schematically, as a computer. The enunciator 56 generates a discernible alarm when the sensors 54 detect nerve stimulation. For example, the enunciator 56 may generate an audible and/or visual alarm signal.

In use, the closure element 18, which may be in the form of a sleeve axially or rotatably arranged relative to the introducer element 12, is moved to a position in which it occludes the opening 16. An incision is made in the patient's body and the introducer element 12 is introduced through the incision. When the tip 14 approaches the spine 58 (FIG. 10) of the patient, the tip 14 is energised to evoke a response from surrounding nerves as the delivery device 10 passes the nerves. In so doing, a clinician is able to inhibit the likelihood of damage being caused to the nerves.

The tip 14 is used to pierce the annulus 24 of the disc 22 to create an opening 60 (FIGS. 2 and 8) in the annulus 24. However, due to the fact that the annulus 24 is of criss-crossed collagen fibres, the applicant is of the view that, rather than breaking the collagen fibres, the fibres will be pushed apart allowing the distal portion of the introducer element 12 to penetrate into the cavity 28 of the disc 22.

When the distal portion of the introducer element 12 is within the cavity 28 of the disc 22, the closure member 18 is manipulated relative to the introducer 12 to open the opening 60. The nucleotomy wire 32 is extended into its bowed configuration (as shown in FIG. 8 of the drawings) in the manner described above. The introducer element 12 is rotated and reciprocated relative to the disc 22 so that the nucleotomy wire 32 dislodges nuclear material within the cavity 28 of the disc 22.

Further, as described above, if necessary, the nucleotomy wire 32 is energised with RF energy to aid in dislodging of nuclear material 30. A suction is applied to the lumen 41 of the introducer element 12 to aid in withdrawal of the nuclear material 30 from the cavity 28 of the disc 22.

Once nuclear material 30 has been removed from the cavity 28 of the disc 22, the nucleotomy wire 32 is withdrawn by unscrewing the control member 34 from the boss 36.

A proximal end of the filler tube 42 is attached to the source of filler material. Prior to the filler material being charged into the interior of the envelope, the filler tube 42 is connected, via a connection 62 (FIG. 2), near its proximal end, to a withdrawal device such as, for example, a syringe. Fluid in the form of air is withdrawn from an interior of the envelope 20 and the filler tube 42 causing both to collapse. Filler material is charged into the interior of the envelope 20 to cause the envelope 20 to be deployed laterally relative to the introducer element 12 through the opening 16, as shown schematically in FIG. 9 of the drawings. Due to the fact that the envelope 20 and filler tube 42 had previously been purged of air, formation of air bubbles in the prosthesis 44 is inhibited.

The envelope 20 is of an elastically deformable material, more particularly, a silicone material. Those skilled in the art will appreciate that the silicone material can expand to one hundred times its unstretched, or relaxed, configuration without plastically deforming. Thus, the filler material, which is also of a silicone material, is charged into the interior of the envelope 20 so that the material over-inflates the envelope 20. This causes distraction of the vertebrae and also allows the envelope 20 to conform to the shape of the cavity 28 once the introducer element 12 has been removed.

The filler material charging into the interior of the envelope 20 causes the envelope 20 to be dislodged from the distal end of the filler tube 42 once the envelope 20 is full. Instead, by appropriate manipulation of the introducer element 12, for example, by rotation, the filled envelope 20 can be detached from the filler tube and accordingly, the delivery device 10.

Regardless of the manner of detachment, once the envelope 20 has been detached from the delivery device 10, the delivery device 10 is removed from the opening 60 in the annulus 24 of the disc 22. As a result of the envelope 20 having been previously over-inflated, removal of the distal portion of the delivery device 10 from within the interior of the disc 22 allows the envelope 20 to conform to the shape of the cavity 28.

It is an advantage of the invention that a self-contained delivery device 10 is provided which can be used both to perform a nucleotomy of a disc 22 as well as to locate a tissue prosthesis 44 within the disc 22. Further, the use of a conductive tip 14 on the delivery device 10 reduces the likelihood of nerve damage when the procedure is carried out.

Still further, the delivery device 10 lends itself to performing such a procedure in a minimally invasive manner and with minimum trauma and discomfort being caused to the patient. It is to be noted that, in general, the stability of a nucleus prosthesis within the annular envelope is dependent on the integrity of the annulus at the time of implantation of the nucleus prosthesis. The annulus may have tears prior to implantation of the prosthesis. However, the size of the annulotomy performed to implant the nucleus prosthesis governs the possibility of extrusion of the prosthesis through the aperture resulting from the annulotomy. Using a finite element analysis model of the intervertebral disc, the applicants have demonstrated that, for an annulotomy aperture of less than 2 mm diameter, the likelihood of extrusion is significantly lower whilst, with a 5 mm diameter annulotomy aperture, the likelihood of extrusion or dislodgement of the prosthesis is greater. The device 10 displaces the fibres of the annulus rather than cutting them (core cut) and this is less likely to cause extrusion as the displaced fibres will tend to assume their initial position on removal of the device 10. Thus, due to the small diameter of the device 10 and the fact that the device 10 tends to displace the fibres of the annulus rather than cutting through them, the likelihood of extrusion of the implanted nucleus prosthesis is reduced.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A self-contained tissue prosthesis delivery device, comprising: an elongate-tubular introducer element, the element including: a tissue separating portion at a distal end, thereof to facilitate the formation of a tissue prosthesis to replace the nucleus of an intervertebral disc without cutting the collagen fibres of an annulus fibrous forming part of the intervertebral disc; a tissue removal portion partially disposed at a proximal end thereof and a distal end thereof, said tissue removal portion including a nucleotomy wire mounted in Longitudinal alignment with the elongate tubular introducer element, said wire being extendible radially outwardly in a bowed configuration from a longitudinally extending opening forming part of said tubular introducer element; a closure member defined by an axially rotatable sleeve member for closing said opening as the introducer element is inserted and introduced within the nucleus of the intervertebral disc and for opening the opening when said tissue removal portion of the introducer element is positioned within the nucleus of the intervertebral disc; an expansible prosthesis envelope received in a collapsed configuration within the tubular introducer element to be deployed laterally of the introducer element through the opening as it is expanded while being charged with a filler material; a coupling member disposed at a distal end of said tubular member for coupling a closed fluid path between the expansible prosthesis envelope and a source of compressible fluid during the nucleotomy and a source of non-compressible fluid during the formation of the tissue prosthesis;

wherein said coupling member includes a generally cylindrically shaped boss member having a centrally disposed threaded aperture in fluid communication with the closed fluid path; and a control member includes a threaded shank dimensioned to be threadably received within said threaded aperture of said coupling member for causing the nucleotomy wire to be in a retracted configuration when said control member is in an extended position relative to said boss and for causing the nucleotomy wire to be deployed in a bowed configuration when said control member is moved into an abutting position relative to said boss.

2. A self-contained delivery device for performing a nucleotomy of an intervertebral disc and for the formation of a tissue prosthesis in place and stead of removed nucleus material, comprising: an elongated tubular member for protectively carrying a collapsed elastically deformable envelope, said tubular member configured to be inserted by fiber displacement through the annulus fibrous and into the nucleus of an intervertebral disc;

a pointed tip disposed at a proximal end of said tubular member for displacing the fibrous material of the annulus fibrous to form a substantially self-closing annulotomy aperture;

a coupling member disposed at a distal end of said tubular member for coupling a closed fluid path between the expansible prosthesis envelope and a source of compressible fluid during the nucleotomy and a source of non-compressible fluid during the formation of the tissue prosthesis; wherein said coupling member includes a generally cylindrically shaped boss member having a centrally disposed threaded aperture in fluid communication with the closed fluid path; a control member includes a threaded shank dimensioned to be threadably received within said threaded aperture of said coupling member for retracting and deploying a nucleotomy wire laterally through a longitudinally oriented opening disposed within said tubular member proximally of said pointed tip; and an axially rotatable sleeve member for closing said opening as the tubular member is inserted by fiber displacement through the annulus fibrous into the nucleus of an intervertebral disc and for opening the opening to facilitate the deployment of the nucleotomy wire to perform the nucleotomy and to facilitate the formation of the tissue prosthesis within the nucleus cavity resulting from the nucleotomy.

3. The self contained delivery device according to claim 2, wherein said pointed tip is a conductive tip for helping to reduce the likelihood of nerve damage while performing the nucleotomy and while forming the tissue prosthesis.

4. The self contained delivery device according to claim 3, wherein said nucleotomy wire is fixed in position within said pointed tip; and wherein said control member threadably separated from said boss member causes the nucleotomy wire to be completely removed from said pointed tip and the self contained device to facilitate the formation of the tissue prosthesis.

5. The self contained device according to claim 2, wherein said a substantially self closing annulotomy aperture has a diameter of less than 5 mm and most preferably a diameter of less than 2 mm.

6. The self contained device according to claim 2, wherein said control member is coupled to said nucleotomy wire; and wherein said control member includes a threaded shank to facilitate the deployment of said wire through said opening for removing nuclear tissue from the intervertebral disc.

7. The self contained delivery device according to claim 2, wherein a tip portion of the nucleotomy wire is shaped to encourage bowing when said control member is threadably received within said boss member.

8. The self contained delivery device according to claim 2, wherein said nucleotomy wire is configured to cooperate with axial rotational movements and rectilinear to and fro movements of the introducer element to facilitate the removal of nucleus material from the nucleus of the intervertebral disc.

9. The self contained delivery device according to claim 2, further comprising:

a filler tube extending along the longitudinal length of the tubular element, wherein said filler tube is coupled between the interior of the elastically deformable envelope and an air withdrawing syringe to form a closed system during the formation of the tissue prosthesis.

10. The self contained delivery device according to claim 9 wherein said filler tube is composed of a flexible material so it will remain collapsed during the performance of the nucleotomy.

11. A self-contained tissue prosthesis delivery device; comprising:

an elongated tubular member for protectively carrying an expansible envelope to help form a tissue prosthesis, said tubular member having a longitudinally disposed opening for the lateral deployment therefrom of a nucleotomy wire to facilitate the performance of a nucleotomy on an intervertebral disc and for the lateral deployment therefrom of the expansible envelope to facilitate the formation of the tissue prosthesis;

an axially rotatable sleeve moveable between a closed position and a closed position, said sleeve in said closed position closing said opening during insertion and placement of said tubular member opening in proper position for the performance of the nucleotomy and said sleeve in said open position opening said opening for deployment of the nucleotomy wire from an overlaying relationship on said expansible envelope to a fully deployed bowed configuration; a coupling member disposed at a distal end of said tubular member for coupling a closed fluid path between the expansible envelope and a source of compressible fluid during the nucleotomy and a source of non-compressible fluid during the formation of the tissue prosthesis; wherein said coupling member includes a generally cylindrically shaped boss member having a centrally disposed threaded aperture in fluid communication with the closed fluid path; and a control member includes a threaded shank dimensioned to be threadably received within said threaded aperture of said coupling member for facilitating the retracting of said nucleotomy wire into the overlaying relationship with the expansible envelope; the lateral deployment of said nucleotomy wire into the fully deployed bowed configuration for the performance of the nucleotomy; and the removal of said nucleotomy wire from the delivery device to facilitate the formation of the tissue prosthesis in a resulting nucleotomy cavity formed in the nucleus of the intervertebral disc.

12. The self contained tissue prosthesis delivery device according to claim 11, further comprising:

an elongated pointed tip disposed distally of said opening for piercing the annulus fibrous of the intervertebral wherein to provide an annulotomy aperture to facilitate the insertion of said tubular member opening in proper position within the nucleus material of the intervertebral disc for the performance of the nucleotomy and formation of the tissue prosthesis;

wherein said annulotomy aperture has a diameter of less than 5 mm and most preferably a diameter of less than 2 mm to facilitate the self closing of said aperture when the delivery device is removed; and wherein said pointed tip is a conductive tip for helping to reduce the likelihood of nerve damage while performing the nucleotomy and while forming the tissue prosthesis.

13. The self contained tissue prosthesis delivery device according to claim 11, further comprising:

an elongated filler tube in fluid communication between the interior of the expansible envelope and a closed source of fluid for collapsing said expansible envelope and another closed source of fluid for expanding said expansible envelope.

14. The self contained tissue prosthesis delivery device according to claim 11, wherein said opening is in fluid communication with a tubular lumen configured along a longitudinal axis of the tubular element, said lumen configured to be in fluid communication with said opening and a source of fluid to facilitate the removal of nucleus material from the intervertebral disc through said opening during the performance of the nucleotomy.

\* \* \* \* \*